(12) United States Patent
Johnson et al.

(10) Patent No.: US 9,345,619 B2
(45) Date of Patent: May 24, 2016

(54) DEVICES, SYSTEMS AND METHODS FOR POSTERIOR SEGMENT DRAINAGE

(71) Applicant: NOVARTIS AG, Basel (CH)

(72) Inventors: Andrew Johnson, Tustin, CA (US); Casey Lind, Orange, CA (US)

(73) Assignee: Novartis AG, Basel (CH)

( * ) Notice: Subject to any disclaimer, the term of this patent is extended or adjusted under 35 U.S.C. 154(b) by 163 days.

(21) Appl. No.: 14/481,990

(22) Filed: Sep. 10, 2014

(65) Prior Publication Data

US 2016/0067093 A1 Mar. 10, 2016

(51) Int. Cl.
 *A61B 19/00* (2006.01)
 *A61F 9/007* (2006.01)

(52) U.S. Cl.
 CPC .................................. *A61F 9/00781* (2013.01)

(58) Field of Classification Search
 CPC .................................................... A61F 9/00781
 USPC ......................................................... 604/8, 9
 See application file for complete search history.

(56) References Cited

U.S. PATENT DOCUMENTS

| | | | | |
|---|---|---|---|---|
| 4,402,681 A * | 9/1983 | Haas | .................... | A61F 9/00781 604/175 |
| 6,050,970 A * | 4/2000 | Baerveldt | ............ | A61F 9/00781 604/10 |
| 7,354,416 B2 * | 4/2008 | Quiroz-Mercado | | A61F 9/00781 604/264 |
| 8,579,848 B2 * | 11/2013 | Field | .................... | A61M 1/0031 604/9 |
| 2012/0089072 A1 * | 4/2012 | Cunningham, Jr. | . | A61F 9/00781 604/9 |
| 2013/0253402 A1 * | 9/2013 | Badawi | ................. | A61F 9/0017 604/8 |

* cited by examiner

*Primary Examiner* — Leslie Deak
(74) *Attorney, Agent, or Firm* — Kenneth D. Bassinger

(57) ABSTRACT

Described herein is a method of implanting a glaucoma drainage device in an eye having a vitreous chamber and a drainage site. The glaucoma drainage device comprises a tube including a lumen extending from an inlet end to an outlet end, and includes a control element that regulates the amount of fluid flow through the glaucoma drainage device. The method comprises implanting the glaucoma drainage device into pars plana tissue from the vitreous chamber, such that the device extends between the vitreous chamber and the drainage site.

12 Claims, 11 Drawing Sheets

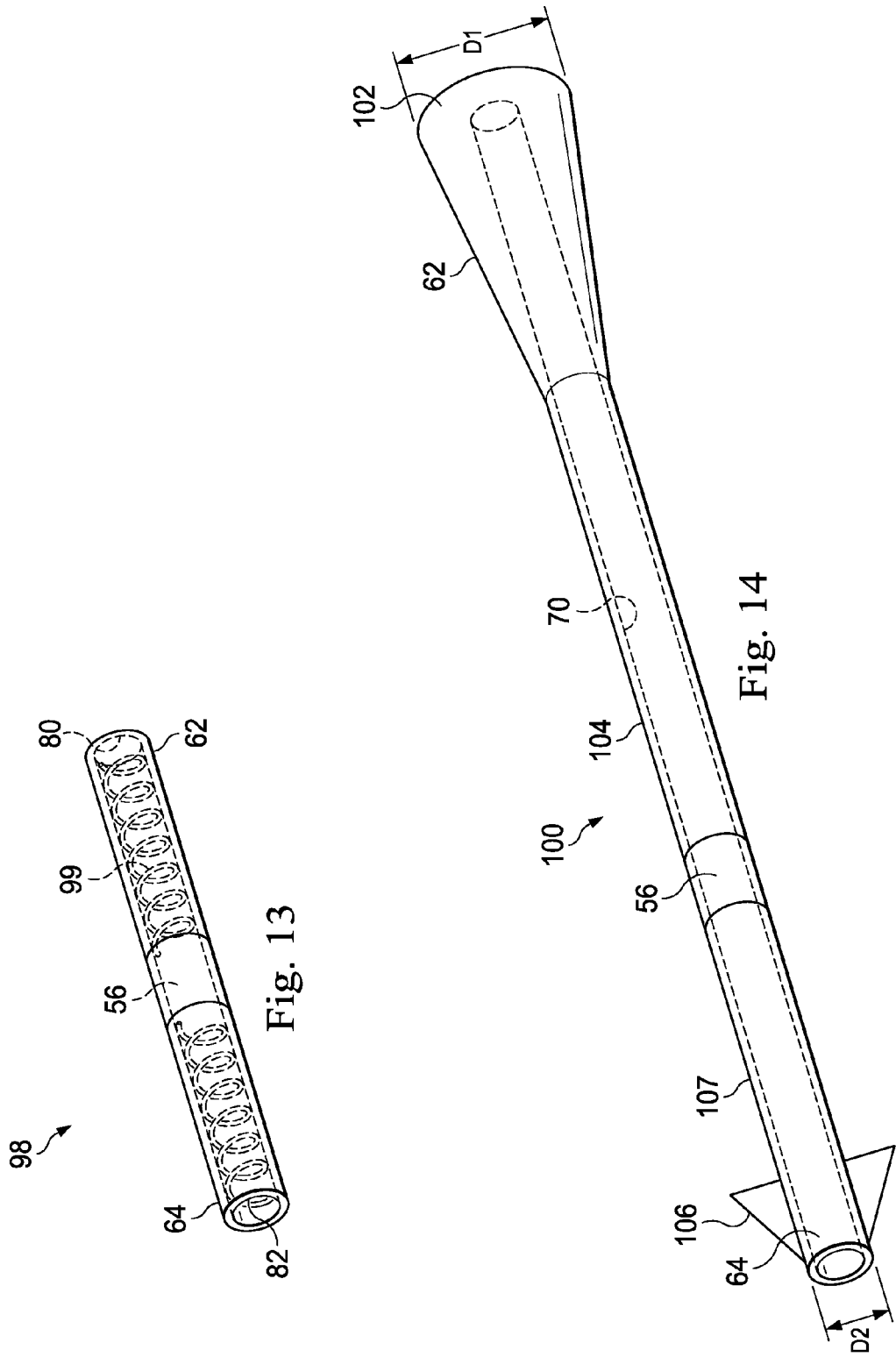

DEVICES, SYSTEMS AND METHODS FOR POSTERIOR SEGMENT DRAINAGE

BACKGROUND

The present disclosure relates generally to pressure/flow control systems and methods for treating a medical condition. In some instances, embodiments of the present disclosure are configured to be part of an IOP control system for the treatment of ophthalmic conditions.

Glaucoma, a group of eye diseases affecting the retina and optic nerve, is one of the leading causes of blindness worldwide. Most forms of glaucoma result when the intraocular pressure (IOP) increases to pressures above normal for prolonged periods of time. IOP can increase due to high resistance to the drainage of the fluid relative to its production. Left untreated, an elevated IOP causes irreversible damage to the optic nerve and retinal fibers resulting in a progressive, permanent loss of vision.

FIG. 1 is a diagram of the front portion of an eye 10 that helps to explain the processes of glaucoma. FIG. 1 shows a representation of the lens 12, cornea 14, iris 16, ciliary body 18, pars plana 20, pars plicata 22, trabecular meshwork 24, Schlemm's canal 26, anterior chamber 28, posterior chamber 30, sclera 32, retina 34, choroid 36, limbus 38, suspensory ligaments or zonules 40, suprachoroidal space 42, conjunctiva 44, and posterior segment 50.

The ciliary body 18 forms an annular ring around and posterior to the lens 12 and lies beneath the iris 16 and adjacent to the lens 12. The ciliary body 18 includes the pars plana 20 and pars plicata 22. The pars plicata 22 contains finger-like projections called ciliary processes and is the anterior portion of the ring that is the ciliary body 18 The pars plana 20 is the posterior portion of this ring. The ciliary body 18 continuously produces clear fluid that fills the anterior segment of the eye 10 (the space between the cornea 14 and lens 12). The fluid washes over the lens 12 and iris 16 and flows out of the anterior chamber 28 (the space between the cornea 14 and iris 16) through the canalicular and the uveoscleral pathways, both of which contribute to the fluid drainage system. The delicate balance between the production and drainage of fluid determines the IOP of the eye 10.

After production by the ciliary body 18, the fluid may leave the eye 10 by several different routes. Some fluid goes posteriorly through the vitreous body behind the lens 12 to the retina 34, while most circulates in the anterior segment of the eye to nourish avascular structures such as the lens 12 and the cornea 14 before outflowing by two major routes: the conventional outflow path 46 and the uveoscleral outflow path 48.

The angle of the anterior chamber 28, which extends circumferentially around the iris 16, contains structures that allow the fluid to drain. The conventional outflow path (or trabecular) route is the main mechanism of outflow, accounting for a large percentage of fluid egress. This route extends from the anterior chamber angle (formed by the iris 16 and the cornea 14), through the trabecular meshwork 24, into Schlemm's canal 26. The trabecular meshwork 24, which extends circumferentially around the anterior chamber 28, is commonly implicated in glaucoma. The trabecular meshwork 24 may act as a filter, limiting the outflow of fluid and providing a back pressure that directly relates to IOP. Schlemm's canal 26 is located just peripheral to the trabecular meshwork 24. Schlemm's canal 26 is fluidically coupled to collector channels (not shown) allowing fluid to flow out of the anterior chamber 28. The arrows 46 show the flow of fluid from the ciliary body 18, over the lens 12, over the iris 16, through the trabecular meshwork 24, and into Schlemm's canal 26 and its collector channels (to eventually reunite with the bloodstream in the episcleral vessels (not shown).

The uveoscleral outflow path 48 accounts for the major remainder of fluid egress in a normal eye 10, and also begins in the anterior chamber angle. Though the anatomy of the uveoscleral route 48 is less clear, fluid is likely absorbed by portions of the peripheral iris 16, and the ciliary body 18, after which it passes into the suprachoroidal space 42. As shown in FIG. 2a, the suprachoroidal space 42 is a potential space of loose connective tissue between the sclera 32 and the choroid 36 that provides a pathway for uveoscleral outflow. Normally the suprachoroidal space 42 is not evident due to the close apposition of the choroid 36 to the sclera 32 from the intraocular pressure of the eye 10. As shown in FIG. 2b, however, the tissues separate to form the suprachoroidal space 42 when fluid accumulates between the tissues. Fluid exits the eye 10 along the length of the suprachoroidal space 42 to eventually reunite with the bloodstream in the episcleral vessels.

One method of treating glaucoma includes implanting a drainage device in a patient's eye. These drainage devices works by bypassing the eye's own trabecular meshwork 24 and instead create an outflow of fluid through a small tube into a drainage site that may be a chamber in the eye 10, space between tissue in and around the eye 10, or a bleb. The drainage device allows fluid to flow from the interior chambers of the eye 10 to a drainage site, relieving pressure in the eye 10 and thus lowering IOP. Drainage devices that drain into the subconjunctival space require that a functional subconjunctival bleb be maintained to allow fluid to be absorbed and drained away. However, subconjunctival blebs are associated with several complications, including bleb failure due to fibrosis, conjunctival leakage, infections, and/or endophthalmitis.

One type of drainage device is the so-called "ab externo, plate style" glaucoma implant. In these ab externo, plate style devices, a flow or drainage tube is inserted into the anterior chamber of the eye 10 from outside the eye 10. A small plate is implanted underneath the conjunctiva 44 to allow flow of fluid out of the eye 10 into the subconjunctival space. These ab externo, plate style devices may require considerable manipulation of the conjunctiva 44 or other drainage site during implantation. Manipulation of these ocular tissues may lead to increased scarring at the delivery site (e.g., the conjunctival bleb), thereby increasing the rate of failure of the drainage device.

Further, inserting drainage devices into the anterior chamber 28 creates the risk of trauma to the cornea 14 or iris 16, which can lead to various adverse events or complications. In addition, tissue within the anterior chamber 28 may occlude the inlet to the drainage device, which can lead to failure of the device.

The system and methods disclosed herein overcome one or more of the deficiencies of the prior art.

SUMMARY

In one aspect, the present disclosure is directed to a method of implanting a glaucoma drainage device in an eye having a vitreous chamber and a drainage site. In one aspect, the glaucoma drainage device comprises a tube including a lumen extending from an inlet end to an outlet end. In one aspect, the drainage device includes a control element that regulates the amount of fluid flow through the glaucoma drainage device. In one aspect, the method comprises implanting the glaucoma drainage device through pars plana tissue from the vitreous chamber, such that the device extends between the vitreous chamber and the drainage site. In one aspect, the method comprises inserting a cannula into the pars plana at a first location in the pars plana tissue, and advancing the glaucoma drainage device through a second location in the pars plana, the second location being separate from the first location. In one aspect, implanting a glaucoma drainage device into the pars plana tissue includes advancing the glaucoma drainage device into the vitreous chamber through the cannula.

In another exemplary aspect, the present disclosure is directed to a method of implanting a glaucoma drainage device in an eye having a vitreous chamber and a drainage site that includes inserting a cannula into a first location of the pars plana. In one aspect, the glaucoma drainage device comprises a tube including a lumen extending from an inlet end to an outlet end. In one aspect, the drainage device includes a control element that regulates the amount of fluid flow through the glaucoma drainage device. In one aspect, the method includes implanting advancing the glaucoma drainage device through the cannula into the vitreous chamber. In one aspect, the method includes implanting, from the vitreous chamber, the glaucoma drainage device into the pars plana tissue between the vitreous chamber and drainage site at a second location different from the first location. In one aspect, inserting a cannula into a first location of the pars plana is performed during a pars plana vitrectomy.

In another exemplary aspect, the present disclosure is directed to a glaucoma drainage device comprising an elongate, hollow tube having a lumen, an inlet end, an outlet end, and an outer diameter. In one aspect, the inlet end comprises a proximal aperture in fluid communication with the lumen for ingress of fluid into the lumen, and the outlet end comprising a distal aperture in fluid communication with the lumen for egress of fluid out of the lumen. In one aspect, the lumen extends from the proximal aperture to the distal aperture. In one aspect, the device comprises a control element having peripheral dimensions sized substantially equal to or smaller than the outer diameter of the tube. In one aspect, the control element is positioned within the lumen of the tube between the inlet end and the outlet end, and is configured to regulate the amount of fluid flow through the glaucoma drainage device.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure. Throughout this description, like elements, in whatever embodiment described, refer to common elements wherever referred to and reference by the same reference number. The characteristics, attributes, functions, interrelations ascribed to a particular element in one location apply to that element when referred to by the same reference number in another location unless specifically stated otherwise. In addition, the exact dimensions and dimensional proportions to conform to specific force, weight, strength and similar requirements will be within the skill of the art after the following description has been read and understood.

All figures are drawn for ease of explanation of the basic teachings of the present invention; the extensions of the figures with respect to number, position, relationship and dimensions of the parts to form examples of the various embodiments will be explained or will be within the skill of the art after the following description has been read and understood.

FIG. 13 is a perspective view of an exemplary embodiment of the glaucoma drainage device showing, in phantom, drainage features according to the principles of the present disclosure.

FIG. 14 is a perspective view of an exemplary embodiment of the glaucoma drainage device having a flared proximal end and retention features according to the principles of the present disclosure.

DETAILED DESCRIPTION

Figure 1:
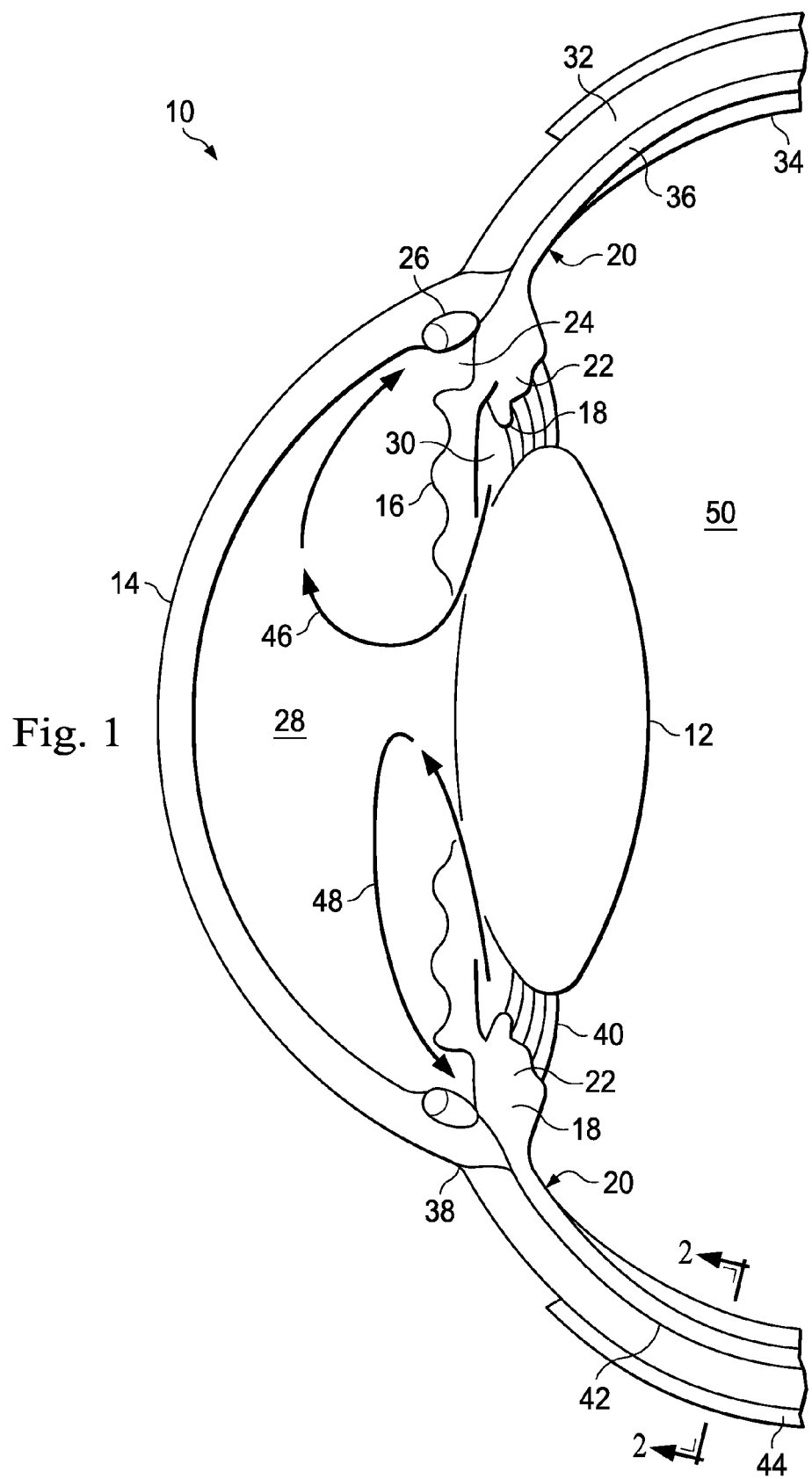
FIG. 1 is a cross-sectional diagram of the front portion of an eye.
Figure 2A:
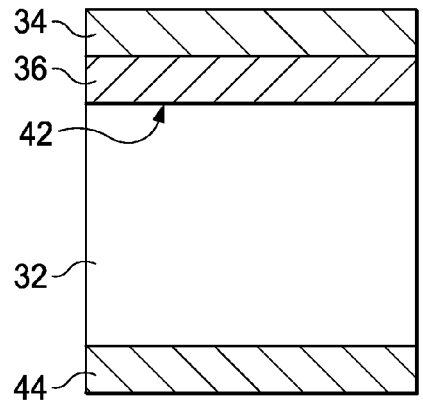
FIGS. 2a and 2b are illustrations of a cross-sectional view of the suprachoroidal space and other associated ocular tissues shown in FIG. 1 (through lines 2-2).
Figure 2B:
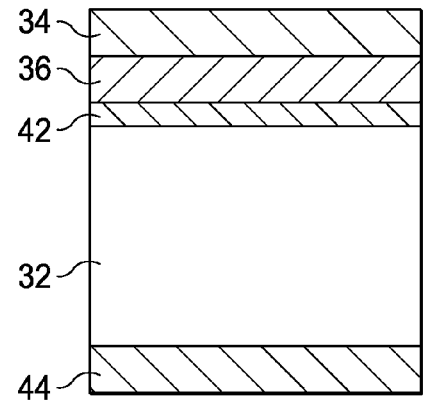

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

The present disclosure is directed to devices and methods of drainage of fluid (e.g., fluid from the vitreous chamber 50) for treating a medical condition, such as glaucoma. In one aspect, the system adjusts IOP by fluid drainage through an implant such as a glaucoma drainage device (GDD)(e.g., the GDD 52 shown in FIG. 3). The system directs fluid drainage from the posterior segment or vitreous chamber 50 of an eye 10 through the glaucoma drainage device to a drainage site 54.

Figure 3:
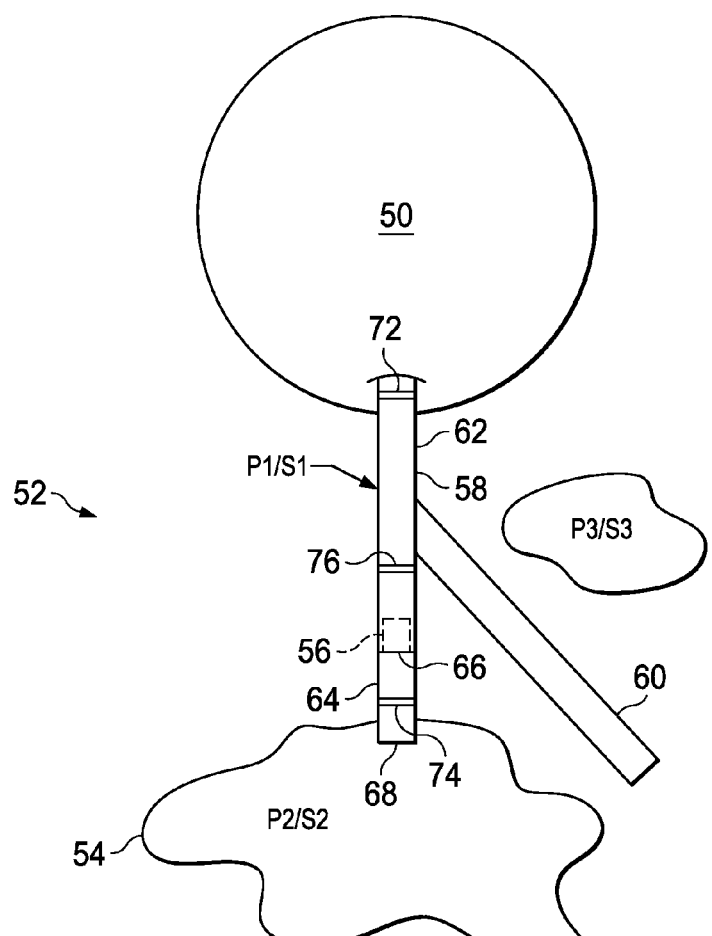
FIG. 3 is a schematic diagram of an exemplary drainage device disposed on an eye according to the principles of the present disclosure.

FIG. 3 is a schematic diagram of an exemplary drainage device or GDD 52 positioned within an eye 10 of a patient. The GDD 52 is designed to regulate IOP by utilizing a flow system 56 (e.g., an adjustable smart valve, passive valve, or active element, without limitation, a pump) to throttle or pump the flow of fluid out of the vitreous chamber 50 through the GDD 52 and into the drainage site 54. Typical drainage sites 54 include the subconjunctival space or the suprachoroidal space 42. Other examples of a drainage site 54 include, but are not limited to: subscleral space, supraciliary space, an episcleral vein, and other uveo-scleral pathways. Thus, the devices, systems, and methods disclosed herein allow the GDD 52 to reside within the tissue of the eye 10 to facilitate draining fluid away from the posterior segment 50 (e.g., the vitreous chamber 50) into the drainage site 54. In these embodiments, the GDD 52 may include any number of valves or pumps, such as are well understood in the art, to regulate the amount of drainage of fluid through the GDD 52.

In this example, the GDD 52 includes a drainage tube 58 and a divider 60 associated with a flow system 56. In some examples, the flow system 56 may be formed as a part of or utilized in a valve system such as those disclosed in patent application Ser. No. 13/315,329, titled "Active Drainage Systems with Pressure-Driven Valves and Electronically-Driven Pump," filed Dec. 9, 2011, which is incorporated herein by reference in its entirety.

The drainage tube 58 drains fluid from the posterior segment 50 of the eye 10 to the drainage site 54. The drainage tube 58 includes an inlet tube 62, which extends from the posterior segment 50 to the flow system 56, and an outlet tube 64, which extends from the flow system 56 to the drainage site 54. The outlet tube 64 includes a proximal end 66 coupled to the flow system 56 and a distal end 68 positioned within the drainage site 54.

In the embodiment pictured in FIG. 3, the GDD 52 is arranged in the eye 10 such that three areas of pressure interact with the implant: P1, P2, and P3. Pressure area P1 reflects the pressure of the posterior segment 50, pressure area P2 reflects the pressure of a drainage site 54, and pressure area P3 reflects a pressure located remotely from P1 and P2 (effectively reflecting atmospheric pressure). In some embodiments, pressure area P1 reflects the pressure located in the inlet tube 62 that is in fluidic communication with the posterior segment 50.

The flow system 56 regulates IOP by throttling or inducing the flow of fluid through the tube 58, from the inlet tube 62 to the outlet tube 64. In some instances, the flow system 56 throttles the flow of fluid through the tube 58 as a function of a pressure differential between the posterior segment 50 and the drainage site 54 or the posterior segment 50 and ambient pressure. The flow system 56 may include components or elements that control pressure by regulating the amount of drainage flow through the GDD 52. The flow system 56 may include any number of valves and/or any number of pumps, or in some embodiments, may not include a pump or a valve. In some embodiments, the flow system 56 is an active system that is responsive to signals from a processor or other control hardware to increase flow, decrease flow, or to maintain a steady flow as a function of pressure differentials across the valve system. In some embodiments, it does this by maintaining a valve setting at a consistent setting, or increasing or decreasing the amount that the valve is open.

In addition, the flow system 56 may incorporate pressure sensors to monitor and utilize the pressures P1, P2, and P3 to achieve a desired IOP via the operation of the GDD 52. In some embodiments, the GDD 52 responds to the pressure differentials between the pressures sensed at P1, P2, and P3 by sensors S1, S2, and S3, respectively, to control the flow system 56 and thereby throttle the flow rate of fluid through the drainage tube 58 to control IOP. In some embodiments, the various pressure differentials across the pressure areas sensed at P1, P2, and P3 (P1-P2, P1-P3, P2-P3) drive the flow system 56 and dictate the valve position or pump state to throttle the flow rate of fluid through the drainage tube 58 to control IOP.

In the embodiment shown in FIG. 3, a pressure sensor S1 measures the pressure in the tube 58 upstream from the flow system 56 and downstream from the posterior segment 50. In this manner, the pressure sensor S1 measures the pressure in the posterior segment 50. The expected measurement discrepancy between the true pressure in the posterior segment 50 and that measured by S1 when located in the tube 58 downstream of the posterior segment 50 is negligible.

A pressure sensor S2 is located at the drainage site 54 or in fluid communication with the drainage site 54 via the outlet tube 64. As such, the pressure sensor S2 may be located in the subconjunctival space, the suprachoroidal space 42, a subscleral space, a supraciliary space, an episcleral vein, or another uveo-scleral pathway, for example.

In some embodiments, the divider 60 acts as a barrier that separates the pressure region measured by the pressure sensor S3 from the pressure region measured by the pressure sensor S2. The divider 60 is a physical structure that separates the drainage site 54 from the isolated location of pressure region measured by the pressure sensor S3. In some embodiments, the flow system 56 includes other barriers that separate the sensors S1, S2, and S3. These barriers may be elements of the flow system 56 itself. In FIG. 3, the pressure region measured by the pressure sensor S3 is physically separated by the divider 60 from the pressure region measured by the pressure sensor S2.

Generally, IOP is a gauge pressure reading—the difference between the absolute pressure in the eye 10 (as measured by sensor S1) and atmospheric pressure (as measured by sensor S3). Atmospheric pressure, typically about 760 mm Hg, often varies in magnitude by 10 mm Hg or more depending on weather conditions or indoor climate control systems. In addition, the effective atmospheric pressure can vary significantly—in excess of 300 mm Hg—if a patient goes swimming, hiking, riding in an airplane, etc. Such variation in atmospheric pressure is significant since IOP is typically in the range of about 15 mm Hg. Thus, for accurate monitoring of IOP, it is desirable to have pressure readings for the posterior segment 50 (as measured by sensor S1) and atmospheric pressure in the vicinity of the eye 10 (as measured by sensor S3).

In one embodiment of the present invention, pressure readings are taken by the pressure sensors S1 and S3 simultaneously or nearly simultaneously over time so that the actual IOP can be calculated (as S1-S3 or S1-f(S3), where f(S3) indicates a function of S3). In another embodiment of the present invention, pressure readings taken by the pressure sensors S1, S2, and S3 can be used to control the flow system 56 that drains fluid from the posterior segment 50. For example, in some instances, the GDD 52 reacts to the pressure differential across S1 and S3 continuously or nearly continuously so that the actual IOP (as S1-S3 or S1-f(S3)) can be responded to accordingly through flow system 56.

In the embodiment of the present invention shown in FIG. 3, pressure readings may be taken by the pressure sensors S1, S2 and S3 or combination of sensors (simultaneously or nearly simultaneously) over time so that the actual IOP can be calculated (e.g., S1-S3). In addition or in the alternative, pressure readings taken by the pressure sensors S1, S2, and S3 are used to control the flow system 56 that drains fluid from the posterior segment 50 as described above. For example, the GDD 52 reacts to the pressure differential across S1 and S2 continuously, nearly continuously or periodically so that a heightened IOP can be responded to by draining fluid from the vitreous chamber 50 to the drainage site 54.

Figure 4:
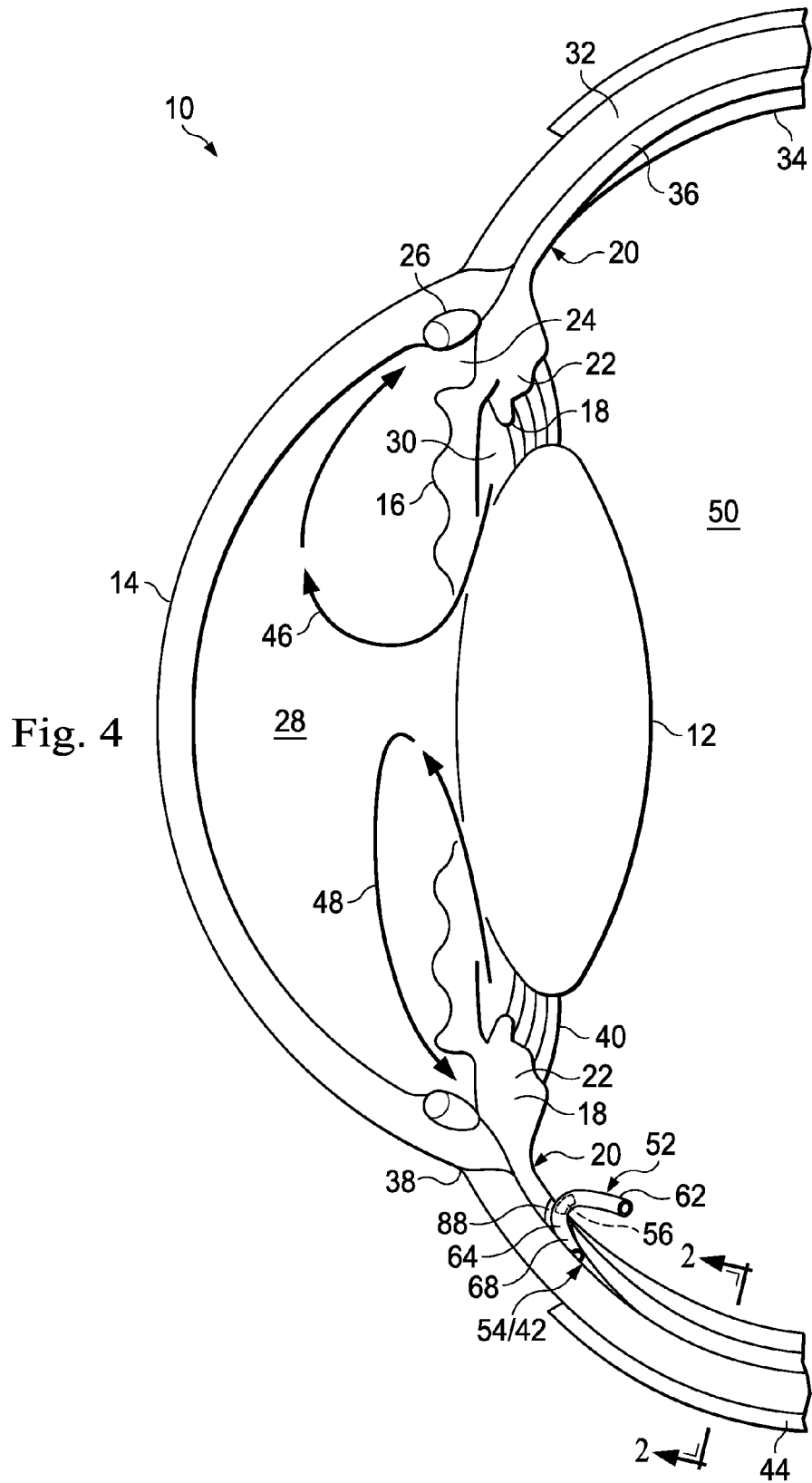
FIG. 4 is a cross-sectional diagram of an exemplary glaucoma drainage device in position in an eye with the outlet tube placed in the suprachoroidal space according to the principles of the present disclosure.
Figure 5:
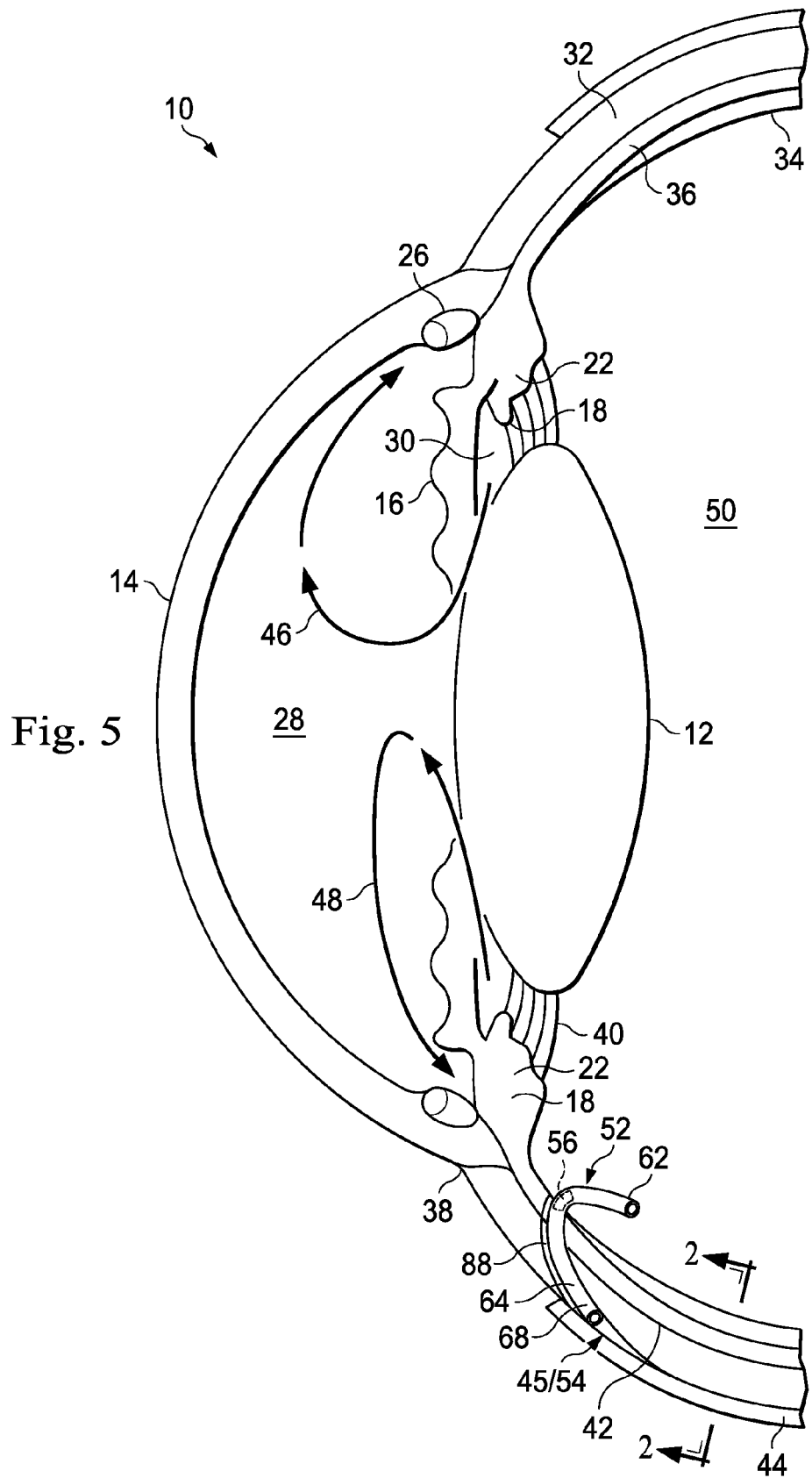
FIG. 5 is a cross-sectional diagram of an exemplary glaucoma drainage device in position in an eye with the outlet tube placed in the subconjunctival space according to the principles of the present disclosure.

FIGS. 4 and 5 are schematic diagrams of the exemplary GDD 52 described above with reference to FIG. 3 positioned within an eye 10 of a patient. In the embodiment pictured in FIG. 4, the GDD 52 is arranged in the eye 10 such that fluid from the posterior segment 50 flows through the GDD 52 to the drainage site 54 (in this case, the suprachoroidal space 42). In the embodiment pictured in FIG. 5, the GDD 52 is positioned within the eye 10 such that fluid from the posterior segment 50 flows through the GDD 52 to the subconjunctival space 45. In these embodiments, the fluid flow from the posterior segment 50 to the drainage site 54 may be determined by pressure differentials across the flow system 56 and/or active control of the GDD 52. For example, in some instances, when the pressure of the vitreous chamber exceeds the pressure of the drainage site 54 (e.g., the subconjunctival/sub-tendon space 45 or the suprachoroidal space 42), this excess pressure causes the flow system 56 to allow or cause fluid to flow from the vitreous chamber 50 to the drainage site 54 thereby reducing this pressure difference. In instances where the flow system 56 moves fluid from the vitreous chamber 50 to the drainage site 54, control parameters set in the flow system 56 may control the amount and rate at which fluid is moved through the GDD 52 depending upon the pressure relationships between P1, P2, and/or P3 (as detected by sensors S1, S2, and S3, respectively).

Figure 6:
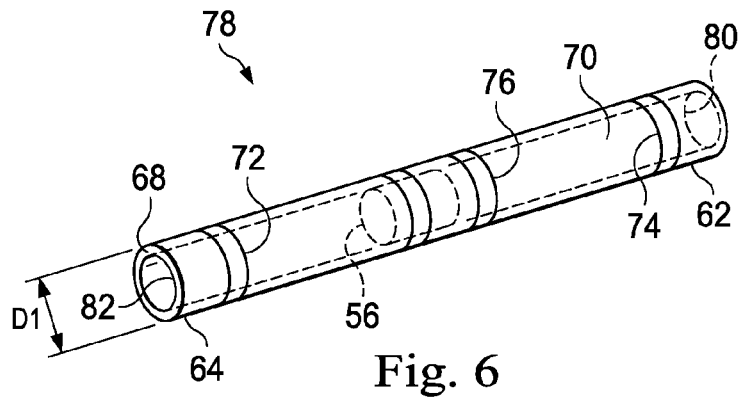
FIG. 6 is a perspective view of an exemplary embodiment of the glaucoma drainage device according to the principles of the present disclosure.
Figure 9:
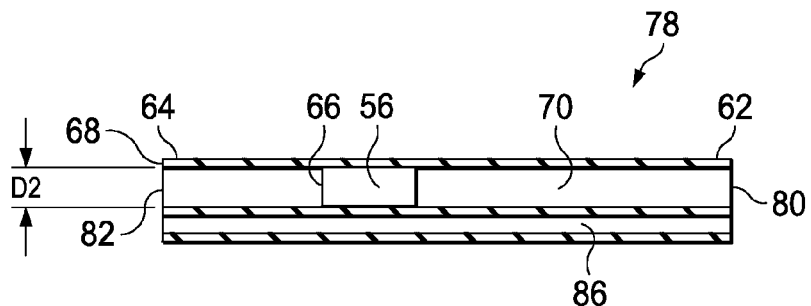
FIG. 9 is a side cross-sectional view of an exemplary embodiment of the glaucoma drainage device having multiple lumens according to the principles of the present disclosure.

As shown in FIG. 6, the GDD 52 includes an outer diameter D1, and the flow system 56 includes peripheral dimensions sized to be equal to or smaller than the outer diameter D1. In some embodiments, as shown in FIG. 9, the peripheral dimensions of the flow system 56 are sized such that the flow system 56 fits entirely within the lumen 70 of the GDD 52. the GDD 52 described herein may be flexible along its entire length, may have a predetermined stiffness along its entire length, or may have a varying degree of stiffness or flexibility along its entire length. Thus, the GDD 52 may be made from any of a variety of flexible, rigid, or composite materials. In particular, the GDD 52 described herein may be made from any of a variety of biocompatible materials having the requisite flexibility and hoop strength for adequate lumen support and drainage through the lumen after implantation. Such materials include, without limitation, silicone tubing, reinforced silicone tubing, PEEK, polycarbonate, or other flexible materials. In some instances, the GDD 52 may be scored or otherwise imprinted for added flexibility throughout the tube or only in one or more portions of the GDD 52.

In any of the embodiments of the GDD 52 described herein, the drainage tube 58 has a lumen 70 extending from the inlet tube 62 to the outlet tube 64 through the flow system 56. The lumen 70 may be coated on its inner surface with one or more drugs or other materials designed to help maintain the patency of the lumen 70. Likewise, any of the embodiments of the GDD 52 described herein may be coated on its outer surface with one or more drugs or other materials designed to encourage healing and/or in-growth of ocular tissue around the GDD 52 to assist in retention of the GDD 52 (e.g., within the tissue between the vitreous chamber 50 and the drainage site 54) or to prevent an immune response to the GDD 52. Such drugs or other materials may also or in the alternative be contained within a polymeric coating applied to the GDD 52.

In embodiments of the GDD 52, the drainage tube 58 has a column strength sufficient to permit the GDD 52 to be inserted into eye 10 such that a distal end 68 of the outlet tube 64 tunnels or is pushed through the ocular tissue without structural collapse or degradation of the GDD 52. In some embodiments, the column strength is sufficient to permit the outlet tube 64 to tunnel through ocular tissues into the drainage site 54 without any structural support from an additional structure such as a delivery device as will be described hereafter.

In all the embodiments of the GDD 52, the drainage tube 58 may include one or more features that aid in properly positioning the GDD 52 in the eye 10. For example, as shown in FIG. 3, the GDD 52 may include markers 72, 74 and 76 comprising positional indicators that can be used to accurately position the GDD 52 in the eye 10. The marker 72 may be positioned adjacent the inlet tube 62 of the GDD 52 and the marker 74 may be positioned adjacent the outlet tube 64 of the GDD 52. The marker 76 may be positioned between the markers 72, 74. In other embodiments, the GDD 52 may include any number and arrangement of markers. The markers 72, 74 and 76 may comprise visual, tomographic, echogenic, or radiopaque markers. In one exemplary method of using the markers to properly position the GDD 52, the outlet tube 64 may be inserted into the drainage site 54 until at least one of the markers 72, 74 or 76 is aligned with an appropriate anatomic structure or surgical indicator (e.g., a suture). For example, a surgeon may advance the outlet tube 64 into the drainage site 54 until the marker 76 aligns with an appropriate anatomic structure, such as, without limitation, the pars plana 20, thereby indicating that an adequate length of the outlet tube 64 has entered the drainage site 54.

As shown in FIG. 4, the GDD 52 is shaped and configured to be implanted within the ocular tissue between the vitreous chamber 50 and the drainage site 54, extending through the pars plana 20. The bulk of the GDD 52 will likely be either in the vitreous chamber 50 or the drainage site 54 of the eye 10; only a small portion of the GDD 52 will pass through the pars plana 20. The GDD 52 may be held in place within the eye 10 via anchoring sutures, the angle of implantation and surrounding anatomy, or by a spring force or other mechanisms that stabilize the GDD 52 relative to the patient's eye 10. In the pictured embodiment, the GDD 52 extends from the vitreous chamber 50 to the drainage site 54.

FIG. 6 shows an exemplary GDD 78 according to one embodiment of the present disclosure. The GDD 78 may be the same as the GDD 52 described above with reference to FIG. 3. In the pictured embodiment, the GDD 78 is shaped and configured as an elongate, flexible, hollow cylinder including an inlet tube 62, an outlet tube 64, and a lumen 70 extending from the inlet tube 62 to the outlet tube 64. The inlet tube 62 is configured to receive fluid from the posterior segment 50 (e.g., the vitreous chamber 50). The outlet tube 64 is configured to allow the egress of fluid into the drainage site 54. The lumen 70 serves as a passageway for the flow of fluid through the GDD 78 from the inlet tube 62, through the outlet tube 64, and into the drainage site 54.

The GDD 78 in some embodiments includes a single proximal aperture 80 at the inlet tube 62 for ingress of fluid and a single distal aperture 82 at the outlet tube 64 for egress of fluid. Both apertures 80, 82 are in communication with the lumen 70. In this embodiment, fluid can flow from the vitreous chamber 50 into the proximal aperture 80 of the inlet tube 62, through the lumen 70, and out the distal aperture 82 of the outlet tube 64 into the drainage site 54.

Figure 7:
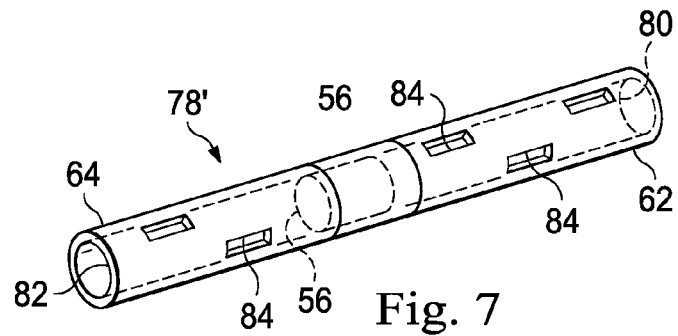
FIG. 7 is perspective view of an exemplary embodiment of the glaucoma drainage device showing multiple apertures according to the principles of the present disclosure.
Figure 8:
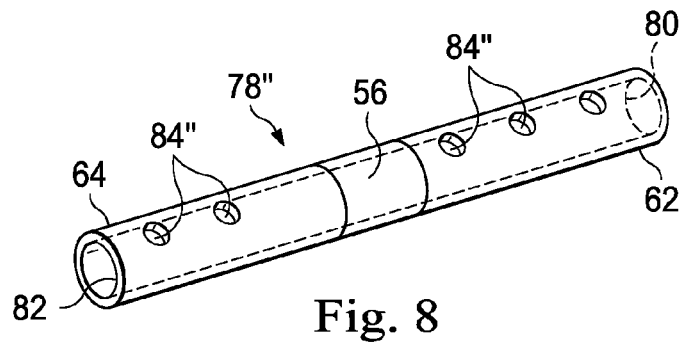
FIG. 8 is perspective view of an exemplary embodiment of the glaucoma drainage device showing multiple apertures according to the principles of the present disclosure.

Various embodiments of the GDD 78 include any number and arrangement of apertures that communicate with the lumen 70. In the exemplary embodiments shown in FIGS. 7 and 8, the GDD 78 includes a plurality of apertures through which fluid may enter and exit the GDD 78. For example, FIGS. 7 and 8 illustrate exemplary GDDs including apertures according to one embodiment of the present disclosure. FIG. 7 illustrates an exemplary GDD 78' according to one embodiment of the present disclosure. In addition to a proximal aperture 80 and a distal aperture 82, both of which are in communication with the lumen 70, the outlet tube 64 includes a plurality of holes 84 located along the length of the outlet tube 64. The holes 84 are in fluid communication with the lumen 70 and allow fluid to enter the lumen 70 at the inlet tube 62 and exit the lumen 70 at the outlet tube 64 and enter the tissues or space surrounding the drainage site 54.

FIG. 8 illustrates an exemplary GDD 78" according to one embodiment of the present disclosure. In addition to a proximal aperture 80 and a distal aperture 82, both of which are in communication with the lumen 70, the outlet tube 64 includes a plurality of holes 84' located along the length of the outlet tube 64. The holes 84" are in fluid communication with the lumen 70 and allow fluid to enter the lumen 70 at the inlet tube 62 and exit the lumen 70 at the outlet tube 64 to enter the tissues or space surrounding the drainage site 54.

In FIG. 7, the illustrated holes 84 are shaped as rectangular apertures. In other embodiments, the holes 84 may have any of a variety of shapes, including, without limitation, circular (as shown by the holes 84" in FIG. 8), ovoid, rhomboid, and square. It should be noted that the spatial configuration, size, and angle of the holes 84 may vary in different embodiments. Multiple apertures or holes 84 in the GDDs 78', 78" guard against the blockage of flow through the GDDs in instances where other holes 84, 84" or apertures may be blocked. In some embodiments, the holes 84, 84" may also function as visual markers to aid in positioning the inlet tube 62 or the outlet tube 64 within the eye 10.

In the embodiment shown in FIG. 7, the holes 84 are interspersed in a staggered pattern along the outlet tube 64 of the GDD 78'. In other embodiments, however, the holes 84 may be arranged in any of a variety of patterns, both asymmetrical and symmetrical, along any portion (or entirety) of the GDD 78'.

In the embodiments shown in FIGS. 6-8, the lumen 70 has a uniform luminal diameter along the length of the GDD 78, 78', 78". In other embodiments described hereafter, the diameter of the lumen 70 varies in diameter along the length of the GDD. Other embodiments may include one or more additional drainage lumens 86 such as is shown in FIG. 9. In the embodiment pictured in FIG. 9, the flow system 56 includes peripheral dimensions that are smaller than or equal to the luminal dimensions (e.g., the luminal diameter D2) of the lumen 70, and the flow system is positioned entirely within the lumen 70.

In exemplary embodiments, the outer diameter of the GDD 78 may range in size from about 0.010 in (0.254 mm) to about 0.040 in (1.016 mm) and more preferably, the outer diameter of the GDD 78 may be about 0.025 in (0.635 mm). However, this disclosure supports GDD 78 of different shapes and dimensions and the GDD 78 of the present disclosure may be of any shape and any dimension that may be accommodated by the eye 10, including the vitreous chamber 50, the drainage site 54, and the tissue therebetween.

Although the GDD 78 is shown having a circular cross-sectional shape, the GDD 78 may have any of a variety of cross-sectional shapes, including without limitation, an ovoid, elliptical, square, rhomboid, or rectangular shape. In some embodiments, the GDD 78 may vary in cross-sectional shape along its length. The particular cross-sectional shape may be selected to facilitate easy insertion into the tissue of the eye 10, and may be dependent upon the method of insertion planned. In some embodiments, the GDD 78 may have a predetermined radius of curvature that conforms to the radius of curvature desirable to reach a desired location in the drainage site 54 from a desired location within the vitreous chamber 50. In other embodiments, the GDD 78 may be sufficiently flexible to conform to the shape of a tunnel 88 (e.g., as in FIG. 4) that may have been created between the vitreous chamber 50 and drainage site 54.

Figure 10:
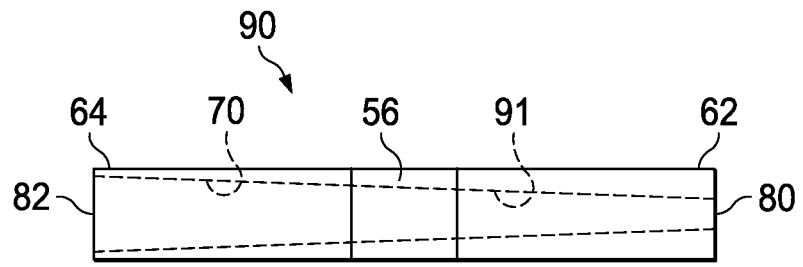
FIG. 10 is a side cross-sectional view of an exemplary embodiment of the glaucoma drainage device having a tapered lumen according to the principles of the present disclosure.

As shown in FIG. 9, in some embodiments the GDD 78 has a substantially uniform outer diameter and a substantially uniform inner diameter of lumen 70 along its entire length. In other embodiments the dimensions of the GDD 78, including the outer diameter and/or the inner diameter of lumen 70, may vary along its length. For example, FIG. 10 illustrates an exemplary GDD 90 that is substantially similar to the GDD 78 except for the differences described herein. In the embodiment shown in FIG. 10, the diameter of the lumen 91 of the GDD 90 tapers from the outlet tube 64 to the inlet tube 62. By having an inner diameter that gradually increases from the inlet tube 62 to the outlet tube 64, a pressure gradient is produced that may help fluid and/or particulate matter that may otherwise clog the GDD 90 to progress toward the distal aperture 82 and exit the GDD 90 through the distal aperture 82.

Other embodiments may have other configurations of varying dimensions. The taper may exist along the entire length of the GDD 90 or may exist along only one or more portions of the GDD 90 (e.g., the distal portion). For example, in other embodiments, the GDD 90 may taper from the inlet tube 62 to the outlet tube 64 or widen in a middle portion of the GDD 90. In exemplary embodiments, the inner diameter of the GDD 90 (i.e., the diameter of the lumen 91) may range in size from about 0.005 in (0.127 mm) to about 0.100 in (2.54 mm). In particular, the inner diameter of the GDD 90 may range in size from about 0.005 in (0.127 mm) to about 0.052 in (1.27 mm) at the proximal aperture 80, and may range in size from about 0.020 in (0.528 mm) to about 0.100 in (2.54 mm) at the distal aperture 82. In one example, the diameter of the lumen 91 may be 0.025 in (0.635 mm) at the proximal aperture 80 and may be about 0.035 in (0.889 mm) at the distal aperture 82.

Figure 11:
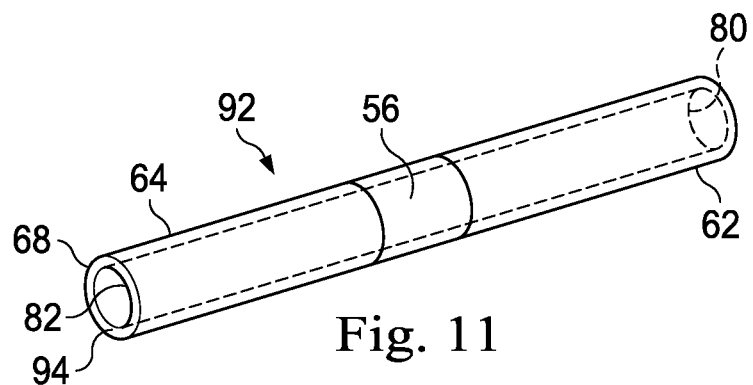
FIG. 11 is a perspective view of an exemplary embodiment of the glaucoma drainage device where the distal end of the outlet tube has a rounded edge according to the principles of the present disclosure.

FIG. 11 shows a GDD 92 according to one embodiment of the present disclosure. The GDD 92 is substantially similar to the GDD 78 except for the differences described herein. In the GDD 92 shown in FIG. 11, the distal end 68 of the outlet tube 64 has an atraumatic shape configured with blunt edges 94 to prevent inadvertent injury to ocular tissues (e.g., the tissue between the vitreous chamber 50 and the drainage site 54) during implantation or if the GDD 90 moves after implantation. In some embodiments, the blunt edges 94 may be shaped in an atraumatic manner such as by having a rounded profile. In some embodiments, the blunt edges 94 may be manufactured of or be coated with a soft material.

Figure 12:
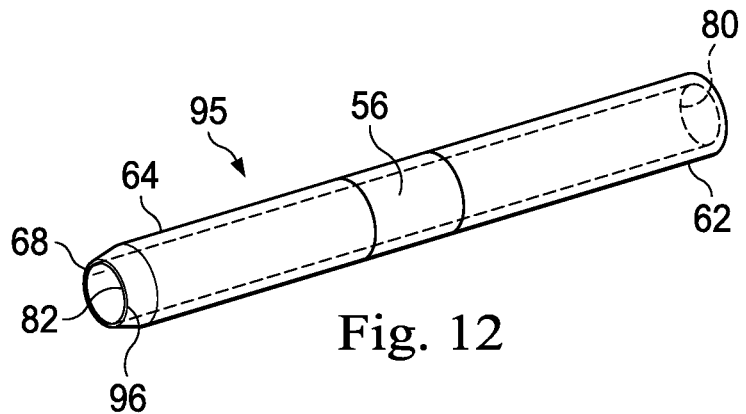
FIG. 12 is a perspective view of an exemplary embodiment of the glaucoma drainage device where the distal end of the outlet tube has a sharpened edge according to the principles of the present disclosure.

FIG. 12 shows a GDD 95 according to one embodiment of the present disclosure. The GDD 95 is substantially similar to the GDD 78 except for the differences described herein. In other embodiments such as those shown in FIG. 12, the outlet tube 64 may be shaped and configured with sharpened edges 96 to permit the outlet tube 64 to pierce ocular tissue (e.g., the pars plana 20) between the vitreous chamber 50 and the drainage site 54 and enter the drainage site 54 without the assistance of a delivery device or a pre-created pathway or tunnel 88 (FIG. 4) through the ocular tissue. For example, in the pictured embodiment, the edges 96 of the outlet tube 64 of the GDD are sufficiently sharp to cut through ocular tissues. In the pictured embodiment, the edges 96 are beveled.

FIG. 13 illustrates a GDD 98 according to another embodiment of the present disclosure. The GDD 98 is substantially similar to the GDD 52 shown in FIG. 3 except for the differences described herein. The GDD 98 includes a plurality of drainage features 99 located along an interior surface of lumen 70. In the pictured embodiment, the drainage features 99 comprise rungs of a spiral shape extending from the proximal aperture 80 to the distal aperture 82. The drainage features 99 are shaped and arranged within the tube to facilitate the passage of fluid through the drainage tube 58 from the proximal aperture 80 to the distal aperture 82. In FIG. 13, the illustrated spiral drainage features 99 are spaced symmetrically along the entire length of the GDD 96. In other embodiments, the drainage features 99 may be arranged asymmetrically, and may be arrayed along only a portion of the GDD 98. In other embodiments, the drainage features 99 may comprise any of a variety of shapes, including, without limitation, protrusions such as nubs or ribs, indentations, dimples, columns, or helices.

An exemplary GDD 100 shown in FIG. 14 has a flared shape at the proximal end 102 of the drainage tube 58 that is designed to prevent the outlet tube 64 from moving further into the drainage site 54 after being properly positioned therein. In particular, the inlet tube 62 has an outer diameter D1 that is wider than the outer diameter D2 of the outlet tube 64 (and the remainder of the GDD 100). The larger diameter D1 allows the inlet tube 62 of the GDD 100 to lodge against tissue within the posterior segment 50 and prevents the GDD 100 from progressing further into the drainage site 54 than desired. Although the inlet tube 62 is relatively cone-shaped, the inlet tube 62 in other embodiments may have any of a variety of shapes designed to prevent the inadvertent progress of the outlet tube 64 past a predetermined space such as the drainage site 54. In some embodiments, a midportion 104 of the GDD 100 may have a larger diameter than the inlet tube 62 and/or the outlet tube 64 of the GDD 100 to lodge against tissue and prevent the outlet tube 64 from moving further into the drainage site 54 after being properly positioned therein.

The GDD 100, in the pictured embodiment, includes retention features 106 that aid in anchoring the GDD 100 within the ocular tissue of an eye 10 (e.g., between the vitreous chamber 50 and drainage site 54) after implantation of the GDD 100. In the exemplary embodiment shown in FIG. 14, the retention features 106 are shaped as wings that protrude from an exterior surface 107 of the outlet tube 64 of the GDD 100. In the pictured embodiment, the retention features 106 are shaped as triangular wings. In other embodiments, the retention features 106 may comprise any of a variety of shapes, including without limitation, helical, rectangular, ovoid, cyclic, round, or combinations thereof. In other embodiments, the retention features may comprise any of a variety of structures, including without limitation, protrusions such as nubs, ribs, or prongs, textured surfaces, and indentations. The retention features 106 are configured to engage with the surrounding tissue and minimize inadvertent movement of the GDD 100 after implantation. The retention features 106 may be flexible or stiff, or have varying degrees of flexibility. In some embodiments, the retention features 106 may include unexpanded and expanded conditions, and may be configured to transition from the unexpanded condition to the expanded condition after final positioning of the GDD 100. The retention features may be made of any of a variety of biocompatible materials, including, by way of non-limiting example, a polymer, Nitinol, or another shape memory material.

FIGS. 15 and 17-22 illustrate exemplary methods of implanting a glaucoma drainage device in any of the embodiments described herein in an eye 10. For purposes of illustration, the method using GDD 52 will be described although the method could be applied to any of the variants of the glaucoma delivery devices GDD 52, GDD 78, GDD 78', GDD 78", GDD 90, gDD 92, GDD 95, or GDD 100. As shown in FIG. 4, the GDD 52 is implanted into the ocular tissue between the vitreous chamber 50 and the drainage site 54 and more specifically through the pars plana 20. The pars plana 20 forms the posterior ring of the ciliary body 18 of the eye 10. Generally, the pars plana 20 ranges in width from 3.5 to 4.0 mm in an adult human eye, and provides an ideal location for insertion of the glaucoma drainage device (e.g., GDD 52). In this position, the GDD 52 allows fluid (e.g., aqueous humour, and/or blood and other fluids) to flow from the vitreous chamber 50 to the drainage site 54 through the GDD 52.

Figure 15:
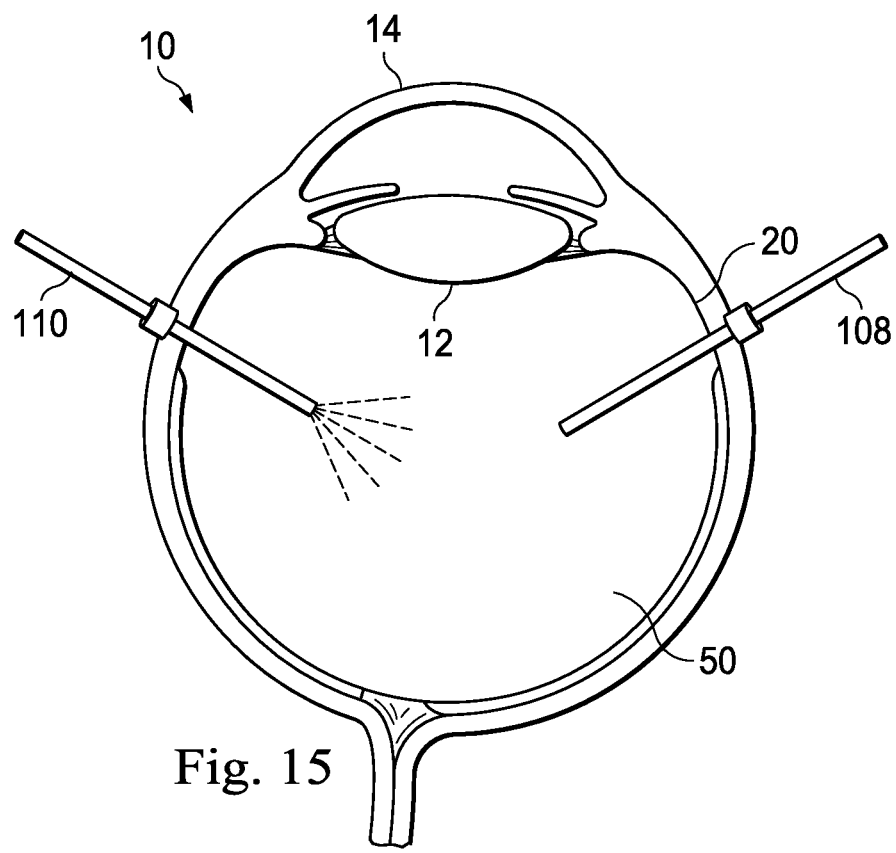
FIG. 15 is a top cross-sectional view of an eye with a cannula and illuminator in place for doing a vitrectomy procedure according to the principles of the present disclosure.

In these methods, typically, the first step is to perform a pars plana vitrectomy to remove the vitreous humour from the eye 10. As shown in FIG. 15, as part of performing the vitrectomy, the surgeon inserts a cannula 108 and an illuminator 110 into the eye 10 on opposite sides of the eye 10 through the pars plana 20. It is desirable to place the instruments used to perform the vitrectomy through the pars plana 20 because entering the eye through the pars plana 20 avoids damage to the retina 34, lens 12 and other sensitive tissues of the eye 10. Although the typical first step in implanting a GDD 52 is to perform a vitrectomy, it may not be required to perform a vitrectomy to implant a GDD 52. The illuminator 110 illuminates the inside of the eye 10. A vitrectomy probe (not shown) placed through the cannula 108 cuts and removes the vitreous humor and/or other fluids or tissues present in the vitreous chamber 50. After the vitrectomy, the cannula 108 is left in place.

Figure 16:
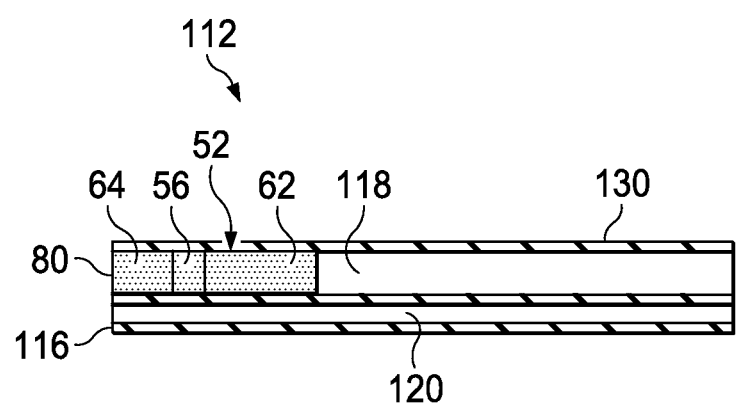
FIG. 16 is a side cross-sectional view of an exemplary delivery device according to the principles of the present disclosure.

An exemplary delivery device 112 is shown in FIG. 16 according to one embodiment of the present disclosure. The delivery device 112 is a cylindrical tube 130 through which the GDD 52 may be placed at a desired location in the eye 10 and may be removed from the eye 10 as desired by the surgeon in a controlled way. The delivery device 112 includes a distal end 116 that may be sharpened and may be articulable so the distal end 116 may be precisely moved into a desired location within the eye 10. The delivery device 112 includes a deployment mechanism 118 that ejects the GDD 52 from the delivery device 112. The delivery device 112 may also include a second lumen 120 through which irrigation, drugs, or other medicaments and/or suction may be applied to the implant site.

Figure 17:
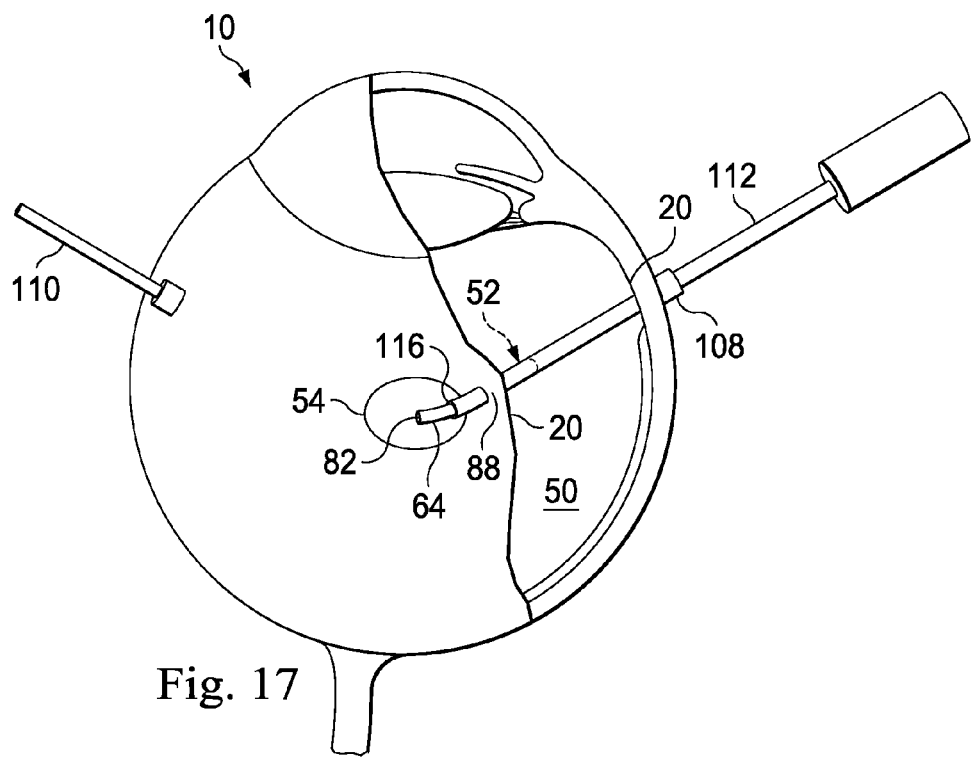
FIG. 17 is a perspective view of an eye with a section removed to show the interior of the eye and also showing an exemplary delivery system delivering an exemplary glaucoma delivery device according to the principles of the present disclosure.
Figure 18:
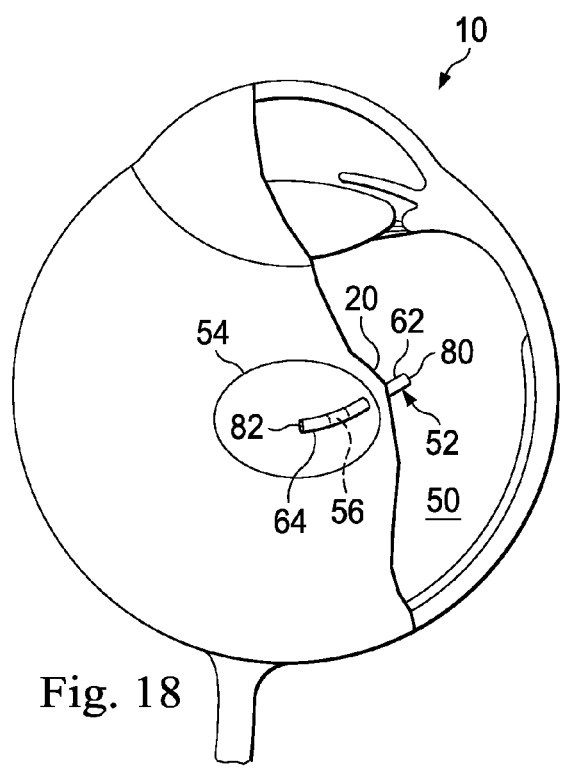
FIG. 18 is a perspective view of an eye with a section removed to show the interior of the eye and also showing the glaucoma delivery device shown in FIG. 17 left in place in the eye according to the principles of the present disclosure.

In the method of placing the GDD 52 shown in FIGS. 17 and 18, the delivery device 112 is used to place the GDD 52 at the appropriate location in the eye 10 extending from the posterior segment 50 (e.g., vitreous chamber 50) to the drainage site 54 through the pars plana 20 and to facilitate the progress of the outlet tube 64 through the pars plana 20 towards and into the drainage site 54. In another method of placing the GDD 52 shown in FIGS. 19 and 20, a surgeon uses one or more surgical instruments to create a pathway or tunnel 88 through the pars plana 20 and into the drainage site 54 for the outlet tube 64 prior to (or during) implantation of the GDD 52. In particular, the surgeon may employ this technique when the outlet tube 64 of the GDD 52 includes blunt or rounded atraumatic edges 94 (as shown in FIG. 11).

FIGS. 17 and 18 illustrate an exemplary method of implanting the GDD 52 in the eye 10 using the delivery device 112. In this method as shown in FIG. 17, the implant delivery device 112 is placed through the cannula 108 (which may have been left in place from a vitrectomy) so that the distal end 116 comes into contact with the tissue of the pars plana 20 at a second location separate from the first location in the pars plana through with the delivery device 112 entered the eye 10. In one embodiment of the delivery device 112, the distal end 116 is sharpened. The surgeon pushes the distal end 116 through the ocular tissue so that the delivery device 112 tunnels through the tissue of the pars plana 20 and forms a tunnel 88. After a tunnel 88 has been formed in the tissue, the GDD 52 is advanced through the tunnel 88 by the delivery device 112 and is positioned in the tunnel 88 so that a desired amount of the outlet tube 64 is located in the drainage site 54 and a desired amount of the inlet tube 62 is located in the vitreous chamber 50. As a result, a relatively small portion of the drainage tube 58 is in contact with the tunnel 88 formed in the ocular tissue of the pars plana 20. Thereafter, the delivery device 112 is removed leaving the GDD 52 in place in the ocular tissue as shown in FIG. 18.

Figure 19:
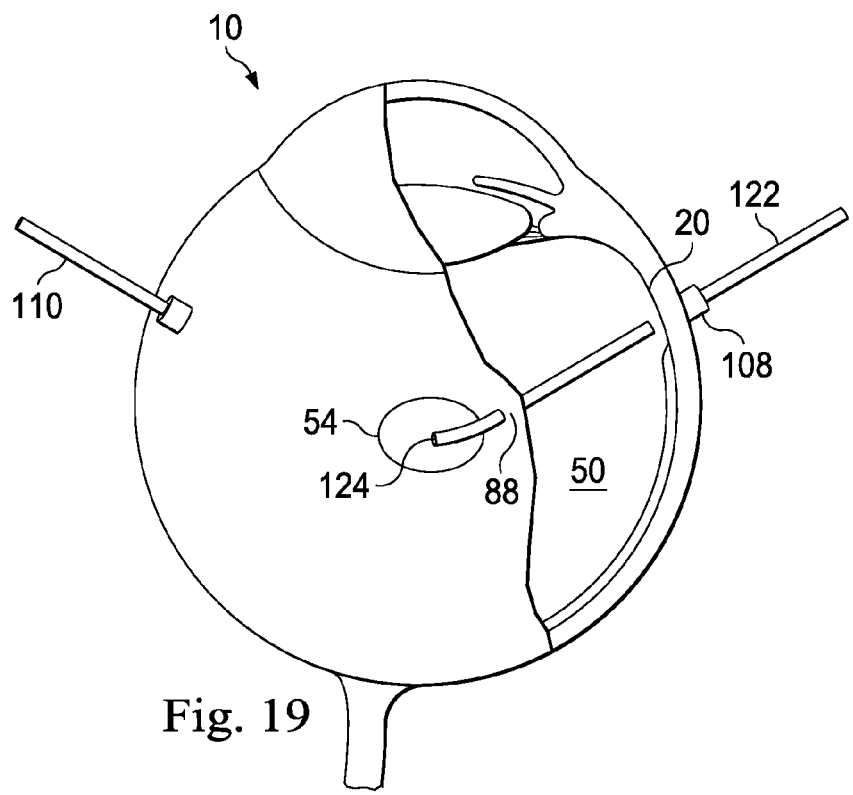
FIG. 19 is a perspective view of an eye with a section removed to show the interior of the eye and also showing an exemplary tunneling instrument forming a tunnel in ocular tissue near a delivery site according to the principles of the present disclosure.
Figure 20:
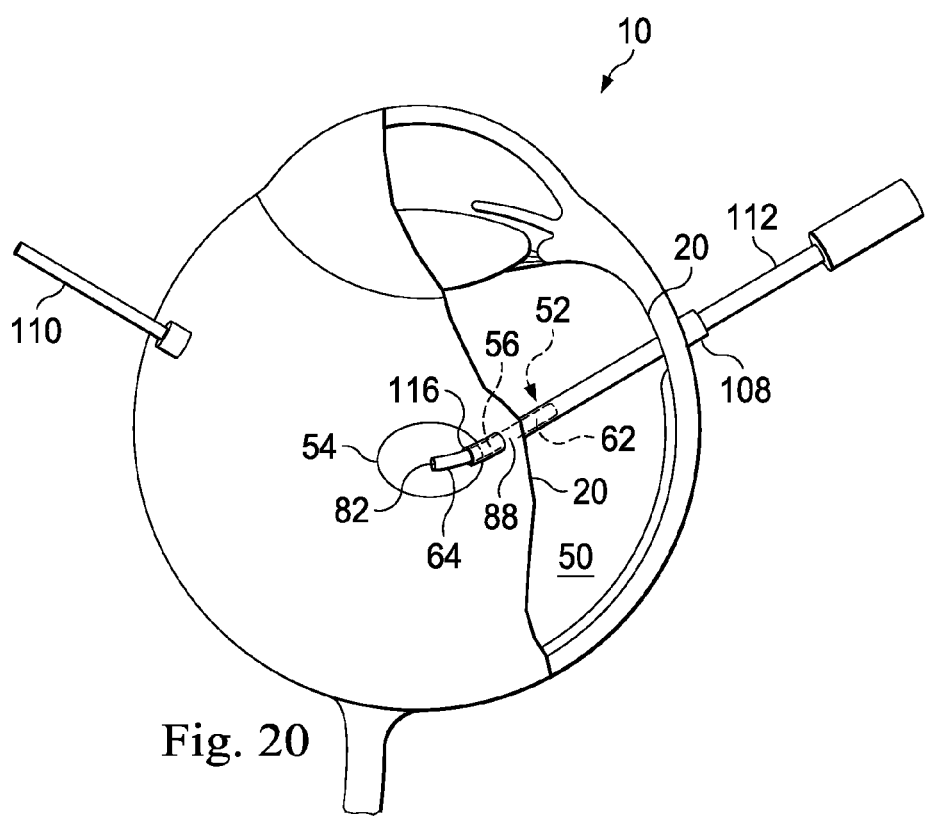
FIG. 20 is a perspective view of an eye with a section removed to show the interior of the eye and also showing an exemplary delivery system delivering an exemplary glaucoma delivery device according to the principles of the present disclosure.

In the method shown in FIGS. 19 and 20, the cannula 108 is left in place from a vitrectomy. The surgeon uses an exemplary tunneling instrument 122 to create a tunnel 88 for implanting the GDD 52. In the method shown in FIGS. 19 and 20, the surgeon inserts a tunneling instrument 122 having a sharpened distal end 124 through the cannula 108 into the vitreous chamber 50. Then, the surgeon creates a tunnel 88 from the vitreous chamber 50 through the pars plana 20 into the drainage site 54 by pushing the sharpened distal end 124 through the ocular tissue from the vitreous chamber 50 thereby creating a tunnel 88 into which the GDD 52 will be placed. In some embodiments, the tunneling instrument 122 may be steerable, articulating, or shapeable in a manner that facilitates the proper approach of the tunneling instrument 122 toward the desired ocular tissues.

Once the tunnel 88 is formed, the tunneling instrument 122 is removed through the cannula 108. Then, as shown in FIG. 20, a delivery device 112 for placing the GDD 52 is placed through the cannula 108 and moved into contact with tunnel 88 as described above. The GDD 52 is pushed or ejected into the tunnel 88 so that the GDD 52 is positioned through the pars plana 20 connecting the vitreous chamber 50 and the drainage site 54 with a desired length of the GDD 52 and the inlet tube 62 protruding into the vitreous chamber 50 and a desired length of the GDD 52 and the outlet tube 64 protruding into the drainage site 54. Then the delivery device 112 and the cannula 108 can be removed from the eye 10 leaving the GDD 52 in place in the ocular tissue as shown in FIG. 18.

Figure 21:
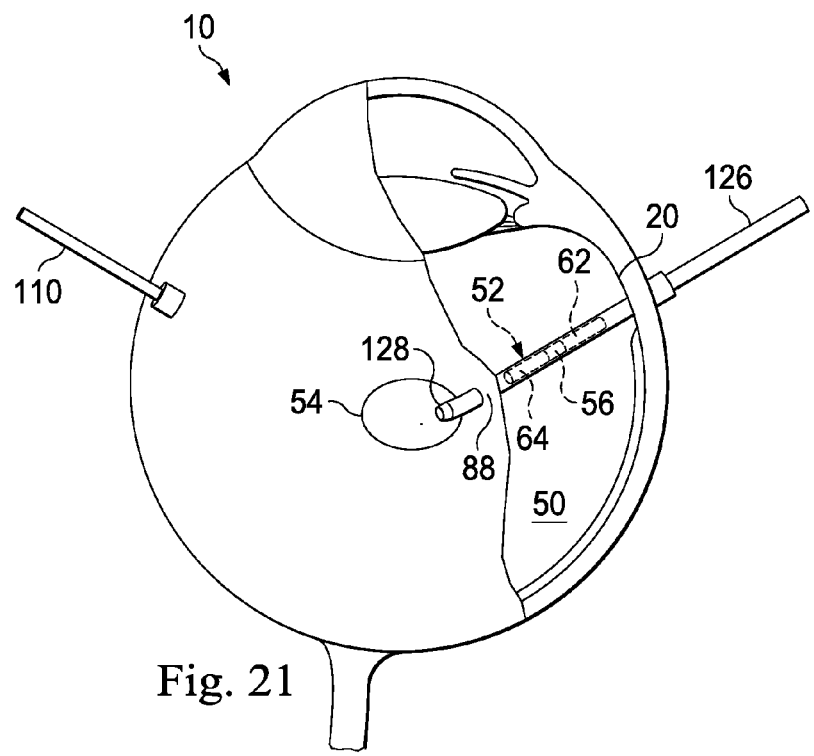
FIG. 21 is a perspective view of an eye with a section removed to show the interior of the eye and also showing an exemplary combination tunneling and delivery instrument for forming a tunnel in ocular tissue near a delivery site according to the principles of the present disclosure.
Figure 22:
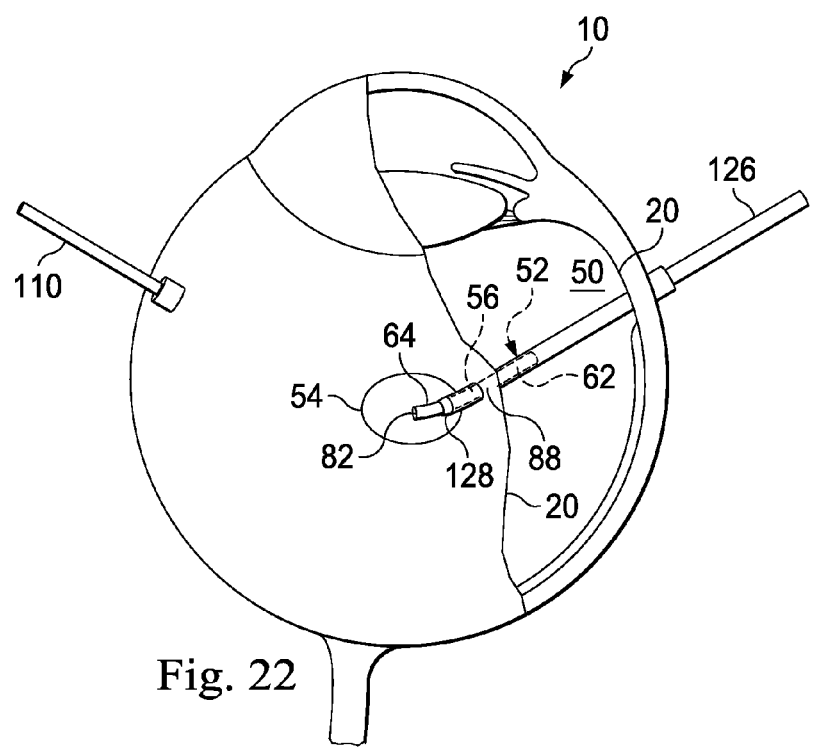
FIG. 22 is a perspective view of an eye with a section removed to show the interior of the eye and also showing the exemplary combination tunneling and delivery instrument of FIG. 21 delivering an exemplary glaucoma delivery device according to the principles of the present disclosure.

In the embodiment shown in FIGS. 21 and 22, there is no cannula 108 left in place from the vitrectomy or there was no vitrectomy performed. In this method, the surgeon uses an exemplary combination tunneling and delivery device 126. This combination device 126 combines the characteristics of the tunneling instrument 122 and the delivery device 112 into a single instrument. The combination device 126 has a sharpened distal end 128. The surgeon inserts the combination device 126 into the vitreous chamber 50, through the pars plana 20. Then, using an ab interno approach, the surgeon creates a tunnel 88 from the vitreous chamber 50 through the pars plana 20 (e.g., on an opposite side of the eye 10) into the drainage site 54 by pushing the sharpened distal end 128 through the pars plana 20 tissue from the vitreous chamber 50 thereby creating a tunnel 88 into which the GDD 52 will be placed. Again, in some embodiments, the combination device 126 may be steerable, articulating, or shapeable in a manner that facilitates the proper approach of the tunneling instrument 122 toward the desired ocular tissues.

Once the tunnel 88 is formed, the delivery device 112 pushes or ejects the GDD 52 into the tunnel 88 so that the GDD 52 is positioned through the pars plana 20 to connect the vitreous chamber 50 and the drainage site 54 with a desired length of the GDD 52 and the inlet tube 62 protruding into the vitreous chamber 50 and a desired length of the GDD 52 and the outlet tube 64 protruding into the drainage site 54. Then, the combination device 126 is removed from the eye 10 leaving the GDD 52 in place in the ocular tissue as shown in FIG. 18.

In another embodiment of the delivery device 112 or combination device 126, the delivery device 112 or the combination device 126 utilizes the GDD 96 shown in FIG. 12, and places the sharpened edges 96 of the outlet tube 64 (as shown in FIG. 12) into contact with the pars plana 20 and pushes the edges 96 of the GDD 95 to cut through the pars plana 20 and create a tunnel 88 and advance the GDD 52 through the tunnel 88. The GDD 52 is positioned in the tunnel 88 so that a desired amount of the outlet tube 64 is located in the drainage site 54 and a desired amount of the inlet tube 62 is located in the vitreous chamber 50 (as shown in FIG. 18). Once the GDD 52 is located in the desired location in the tunnel 88, the delivery device 112 or the combination device 126 is removed, leaving the GDD 52 in place in the ocular tissue as shown in FIG. 18.

The ab interno (from the inside of the eye) approach described herein, which discloses placing the GDD of the present disclosure in the tissue of the pars plana 20 from the interior of the eye 10, minimizes the trauma to the tissue of the eye 10 compared to the traditional ab externo approach. In addition, the ab interno approach disclosed herein may avoid several of the adverse events common with traditional devices and methods for draining excess fluid from the interior of the eye, including from the vitreous chamber 50. The trauma to the ocular tissue is minimized in the ab interno approach because there is no need to manipulate the implant site from outside the eye 10 near the implant site. For example, the ab interno approach described herein may avoid damage to a subconjunctival drainage site due to possible over-manipulation of the tissue (e.g., which might happen during an ab externo delivery approach).

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

We claim:

1. A method of implanting a glaucoma drainage device in an eye having a vitreous chamber and a drainage site, the glaucoma drainage device comprising a tube, the tube including a lumen extending from an inlet end to an outlet end, the drainage device including a control element that regulates the amount of fluid flow through the glaucoma drainage device, the method comprising:
   implanting, from the vitreous chamber, the glaucoma drainage device into pars plana tissue to extend between the vitreous chamber and the drainage site;
   further comprising inserting a cannula into the pars plana at a first location in the pars plana tissue; wherein implanting a glaucoma drainage device into the pars plana tissue includes advancing the glaucoma drainage device into the vitreous chamber through the cannula;
   further comprising the steps of: providing a delivery device having a distal end;
   advancing the distal end through the cannula until the distal end comes into contact with ocular tissue of the pars plana at a second location in the pars plana separate from the first location;
   pushing the distal end through the ocular tissue at the second location so that the delivery device penetrates the tissue of the pars plana to form a tunnel;
   advancing the glaucoma drainage device through the delivery device into the tunnel; and
   positioning the glaucoma drainage device in the tunnel so that a desired amount of the outlet end is located in the drainage site and a desired amount of the net end is located in the vitreous chamber.

2. The method of claim 1 wherein implanting a glaucoma drainage device into the pars plana tissue includes advancing the glaucoma drainage device through a second location in the pars plana, the second location being separate from the first location.

3. The method of claim 1 further comprising:
   providing a tunneling instrument having a first distal end;
   advancing the first distal end through the cannula until the first distal end comes into contact with ocular tissue of the pars plana at a second location separate from the first location;
   pushing the first distal end through the ocular tissue at the second location so that the tunneling instrument advances through the ocular tissue of the pars plana to form a tunnel;
   removing the tunneling instrument through the cannula;
   placing a delivery device having a second distal end through the cannula so that the second distal end comes into contact with the tunnel at the second location in the pars plana;
   advancing the glaucoma drainage device through the drainage device into the tunnel; and
   positioning the glaucoma drainage device in the tunnel so that a desired amount of the outlet end is located in the drainage site and a desired amount of the inlet end is located in the vitreous chamber.

4. The method of claim 1 further comprising:
   providing a combination tunneling and delivery device, the combination device having a distal end;
   inserting the combination device from outside the eye into the vitreous chamber through a first location in the pars plana tissue;
   advancing the distal end into contact with the tissue of the pars plana at a second location separate from the first location;
   advancing the distal end through the pars plana tissue at the second location to form a tunnel through ocular tissue;
   advancing the glaucoma drainage device through the combination device into the tunnel; and
   positioning the glaucoma drainage device in the tunnel so that a desired amount of the outlet end is located in the drainage site and a desired amount of the inlet end is located in the vitreous chamber.

5. The method of claim 1 wherein implanting a glaucoma drainage device into the pars plana tissue between the vitreous chamber and drainage site includes:
   advancing the outlet end through ocular tissue of the pars plana so that the glaucoma drainage device tunnels through the ocular tissue to form a tunnel through the pars plana;
   advancing the glaucoma drainage device into the tunnel; and
   positioning the glaucoma drainage device in the tunnel so that a desired amount of the outlet end is located in the drainage site and a desired amount of the inlet end is located in the vitreous chamber.

6. The method of claim 5 further comprising:
   placing the glaucoma delivery device into the vitreous chamber through a first location in the pars plana tissue; and
   implanting the glaucoma drainage device at a second location in the pars plana separate from the first location.

7. The method of claim 1 further comprising:
   placing the glaucoma delivery device into the vitreous chamber through a first location in the pars plana tissue; and
   implanting the glaucoma drainage device at a second location in the pars plana separate from the first location.

8. The method of claim 1 further comprising:
   providing a delivery device having a distal end;
   advancing the distal end through a first location in the pars plana tissue into the posterior segment;

advancing the distal end until the distal end comes into contact with ocular tissue of the pars plana at a second location separate from the first location;

advancing the distal end through the ocular tissue at the second location forms a tunnel through the pars plana;

advancing the glaucoma drainage device through the delivery device into the tunnel; and positioning the glaucoma drainage device in the tunnel so that a desired amount of the outlet end is located in the drainage site and a desired amount of the inlet end is located in the vitreous chamber.

9. The method of claim 1 further comprising the step of:

providing a tunneling instrument having a first distal end;

advancing the first distal end through a first location in the pars plana;

advancing the first distal end through the posterior segment until the first distal end comes into contact with a second location in the pars plana separate from the first location;

advancing the tunneling instrument through ocular tissue at the second location of the pars plana to form a tunnel;

removing the tunneling instrument;

placing a delivery device having a second distal end through the first location in the pars plana;

advancing the second distal end through the posterior segment until the second distal end comes into contact with the tunnel at second location in the pars plana;

advancing the glaucoma drainage device through the delivery device into the tunnel; and positioning the glaucoma drainage device in the tunnel so that a desired amount of the outlet end is located in the drainage site and a desired amount of the inlet end is located in the vitreous chamber.

10. A method of implanting a glaucoma drainage device in an eye having a vitreous chamber and a drainage site, the glaucoma drainage device comprising a tube, the tube including a lumen extending from an inlet end to an outlet end, the drainage device including a control element that regulates the amount of fluid flow through the glaucoma drainage device, the method comprising:

inserting a cannula into a first location of the pars plana; and implanting, from the vitreous chamber, the glaucoma drainage device into the pars plana tissue between the vitreous chamber and drainage site at a second location different from the first location, by advancing the glaucoma drainage device through the cannula into the vitreous chamber;

further comprising the steps of: providing a delivery device having a distal end;

advancing the distal end through the cannula until the distal end comes into contact with ocular tissue of the pars plana at the second location;

pushing the distal end through the ocular tissue at the second location in the pars plana so that the delivery device forms a tunnel through the pars plana;

advancing the glaucoma drainage device through the delivery device into the tunnel; and positioning the glaucoma drainage device in the tunnel so that a desired amount of the outlet end is located in the drainage site and a desired amount of the net end is located in the vitreous chamber.

11. The method of claim 10 wherein inserting a cannula into a first location of the pars plana is performed during a pars plana vitrectomy.

12. The method of claim 10 further comprising the step of:

providing a tunneling instrument having a first distal end;

advancing the first distal end through the cannula until the first distal end comes into contact with ocular tissue of the pars plana at a second location separate from the first location;

pushing the first distal end through the ocular tissue at the second location so that the tunneling instrument advances through the ocular tissue of the pars plana to form a tunnel;

removing the tunneling instrument through the cannula;

placing a delivery device having a second distal end through the cannula so that the second distal end comes into contact with the tunnel at the second location in the pars plana;

advancing the glaucoma drainage device through the drainage device into the tunnel; and positioning the glaucoma drainage device in the tunnel so that a desired amount of the outlet end is located in the drainage site and a desired amount of the inlet end is located in the vitreous chamber.

* * * * *